(12) United States Patent
Liu

(10) Patent No.: US 7,268,231 B2
(45) Date of Patent: Sep. 11, 2007

(54) 1,5-NAPHTHYRIDINE AZOLINONE

(75) Inventor: Jin-Jun Liu, Warren Township, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 83 days.

(21) Appl. No.: 11/244,022

(22) Filed: Oct. 5, 2005

(65) Prior Publication Data

US 2006/0084673 A1 Apr. 20, 2006

Related U.S. Application Data

(60) Provisional application No. 60/618,807, filed on Oct. 14, 2004.

(51) Int. Cl.
*C07D 471/02* (2006.01)

(52) U.S. Cl. .................................................... 546/122
(58) Field of Classification Search ................. 546/122
See application file for complete search history.

(56) References Cited

FOREIGN PATENT DOCUMENTS

WO   WO 2004/047760 A2   6/2004

OTHER PUBLICATIONS

Camille G. Wermuth, Practice of Medicinal Chemistry, pp. 203-237 (1996).

*Primary Examiner*—D. Margaret Seaman
*Assistant Examiner*—Nizal S. Chandrakumar
(74) *Attorney, Agent, or Firm*—George W. Johnston; Patricia S. Rocha-Tramaloni; David E. Wildman

(57) ABSTRACT

1,5-Naphthyridine azolinone derivatives are disclosed. These compounds are inhibitors of CDK1 and are useful as antiproliferative agents, such as anti-cancer agents.

30 Claims, No Drawings

1,5-NAPHTHYRIDINE AZOLINONE

PRIORITY TO RELATED APPLICATIONS

This application claims the benefit of U.S. Provisional Application No. 60/618,807, filed Oct. 14, 2004, which is hereby incorporated by reference in its entirety.

FIELD OF THE INVENTION

The field of this invention relates to 1,5-Naphthyridine azolinone derivatives which demonstrates CDK1 antiproliferative activity and are useful as anti-cancer agents.

BACKGROUND OF THE INVENTION

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. (See, e.g., the articles compiled in *Science*, 274:1643-1677 (1996); and *Ann. Rev. Cell Dev. Biol.*, 13:261-291 (1997)). CDK complexes are formed through association of a regulatory cyclin subunit (e.g., cyclin A, B1, B2, D1, D2, D3 and E) and a catalytic kinase subunit (e.g., CDK1, CDK2, CDK4, CDK5 and CDK6). As the name implies, the CDKs display an absolute dependence on the cyclin subunit in order to phosphorylate their target substrates, and different kinase/cyclin pairs function to regulate progression through specific phases of the cell-cycle.

As seen above, these protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

Because CDKs such as CDK1 serve as general activators of cell division, inhibitors of CDK1 can be used as antiproliferative agents. These inhibitors can be used for developing therapeutic intervention in suppressing deregulated cell cycle progression.

SUMMARY OF THE INVENTION

In accordance with this invention, it has been discovered that compounds of the formula:

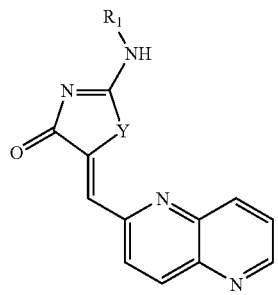

wherein
Y is —S— or —NH—;
$R_1$ is a member selected from the group consisting of hydrogen, lower alkyl, cyclolower alkyl, lower alkoxy-lower alkyl,

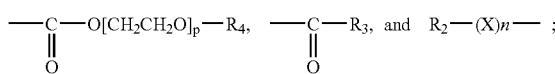

$R_3$ is a member selected from selected from hydrogen, lower alkyl, cyclolower alkyl containing from 3 to 6 carbon atoms and

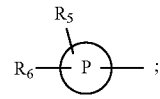

$R_4$ is hydrogen or lower alkyl;
X is a member selected from the group consisting of lower alkylene, hydroxyloweralkylene, cycloloweralkylene, and mono- or di-halo lower alkylene;

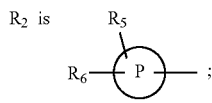

is a member selected from the group consisting of an aryl ring, a 4 to 6 membered heterocycloalkyl ring containing from 3 to 5 carbon atoms and from 1 to 2 hetero atoms selected from the group consisting of oxygen, nitrogen and sulfur, and a 5 or 6 membered heteroaromatic ring containing from 1 to 2 hetero atoms selected from the group consisting of oxygen, sulfur and nitrogen;

$R_5$ and $R_6$ are independently selected from the group consisting of hydroxy, hydroxy-lower alkyl, hydrogen, lower alkyl, halogen, perfluro lower alkyl and lower alkoxy;

n is an integer from 1 to 2; and p is an integer from 0 to 6;

N-oxides thereof where $R_2$ contains a nitrogen in the heteroaromatic ring, sulfones thereof where $R_2$ contains a sulfur in the heterocycloalkyl ring or heteroaromatic ring, and pharmaceutically acceptable salts thereof, inhibit the activity of CDKs, particularly CDK1. These inventive agents and pharmaceutical compositions containing such agents are useful in treating various diseases or disorder states associated with uncontrolled or unwanted cellular proliferation, such as cancer, autoimmune diseases, viral diseases, fungal diseases, neurodegenerative disorders and cardiovascular diseases.

Inhibiting and/or modulating the activity of CDKs, particularly CDK1, makes these compounds of formula and compositions containing these compounds useful in treating diseases medicated by kinase activity, particularly as anti-tumor agents in treating cancers.

DETAILED DESCRIPTION OF THE INVENTION

As pointed out herein, the compounds of Formula I are potential anti-proliferation agents and are useful for mediating and/or inhibiting the activity of CDKs, particularly CDK1, thus providing anti-tumor agents for treatment of cancer or other diseases associated with uncontrolled or abnormal cell proliferation.

Among the preferred compounds of Formula I are the compounds of the formula:

I-A wherein $R_1'$ is a member selected from the group consisting of hydrogen, lower alkyl, cyclolower alkyl, lower alkoxy-lower alkyl, —C(=O)—O[CH$_2$CH$_2$O]$_p$—R$_4$ and —C(=O)—R$_3$; and Y, $R_3$, $R_4$ and p are as above;

and pharmaceutically acceptable salts thereof, and compounds of the formula:

I-B wherein
$R_1''$ is $R_2$—(X)$_n$—; Y, n, $R_2$ and X are as above;

N-oxides thereof where $R_2$ contains a nitrogen in the heteroaromatic ring, sulfones thereof where $R_2$ contains a sulfur in the hetero ring or heteroaromatic ring, and pharmaceutically acceptable salts thereof.

In compounds I and I-B, where $R_1$, and $R_1''$ contain an aryl moiety, the preferred aryl moiety is substituted phenyl. As used herein, the halogen includes all four halogens such as chlorine, fluorine, bromine and iodine.

As used in the specification, the term "lower alkyl", alone or in combination, means a monovalent straight or branched-chain saturated hydrocarbon alkyl group containing from one to six carbon atoms, such as methyl, ethyl, n-propyl, isopropyl, n-butyl, sec-butyl, isobutyl, tert-butyl, n-pentyl, n-hexyl and the like.

The term "cycloalkyl" means a cyclolower alkyl substituent which designates a monovalent unsubstituted 3- to 6-membered saturated carbocylic hydrocarbon ring. Among the preferred cycloalkyl substituents are cyclopropyl, cyclobutyl, cyclohexyl, etc., with cyclopropyl being especially preferred.

The term "lower alkoxy" means a straight-chain or branched-chain alkoxy group formed from lower alkyl containing form one to six carbon atoms, such as methoxy, ethoxy, n-propoxy, isopropoxy, n-butoxy, tert-butoxy and the like.

The term "aryl" means a monovalent mono- or bicyclic unsubstituted aromatic hydrocarbon ring, such as phenyl or naphthyl, with phenyl being preferred.

The term "heterocycloalkyl" refers to a 4 to 6 membered monocyclic saturated ring containing 3 to 5 carbon atoms and one or two hetero atoms selected from the group consisting of oxygen, nitrogen or sulfur. Among the preferred heterocyclic alkyl groups are included mopholinyl, thiopyranyl or tetrahydro pyranyl.

The term "heteroaromatic ring" refers to a monovalent 5 or 6 membered monocyclic heteroaromatic ring containing from 4 to 5 carbon atoms and from 1 to 2 hetero atoms selected from the group consisting of oxygen, nitrogen or sulfur. Among the preferred heteroaromatic groups are included thiopenyl, thioazole, pyridinyl, furanyl, etc.

The term "hydroxy" or "hydroxyl" means —OH.

The term "hydroxy lower alkyl" means a lower alkyl group, as defined above, which is substituted, preferably monosubstituted, by a hydroxy group.

The term "lower alkylene" designates a divalent saturated straight or branch chain hydrocarbon substituent containing from one to six carbon atoms.

The term "cyclo lower alkylene" designates a cyclo lower alkenyl substituent which is a divalent unsubstituted 3 to 6 membered saturated carbocyclic hydrocarbon ring. Among the preferred cycloalkylene substituents are cyclopropenyl and cyclobutenyl.

The term "lower alkanoyloxy lower alkylene" designates a lower alkylene substituent substituted, preferably monosubstituted, with a lower alkanoyloxy group where lower alkanoyloxy is defined as above.

The term "lower alkoxy-lower alkylene" denotes a lower alkylene substituent, as designated hereinbefore, substituted, preferably monosubstituted, with a lower alkoxy group, where lower alkoxy is defined as above.

The term "hydroxy lower alkylene" designates a lower alkylene substituent substituted, preferably monosubstituted, with a hydroxy group.

The term "lower alkoxy-lower alkyl" means a lower alkyl substituent as defined above which is substituted, preferably monosubstitued, with a lower alkoxy group, wherein the lower alkoxy group is as defined above.

The term "perfluoro-lower alkyl" means any lower alkyl group wherein all the hydrogens of the lower alkyl group are substituted or replaced by fluorine. Among the preferred perfluoro-lower alkyl groups are trifluoromethyl, pentafluoroethyl, heptafluoropropyl, with trifluoromethyl being especially preferred.

The term "pharmaceutically acceptable salts" refers to conventional acid-addition salts or base-addition salts that retain the biological effectiveness and properties of the compounds of Formulas I, II, III, IV and V and are formed from suitable non-toxic organic or inorganic acids, or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Exemplary base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456-1457.

The compounds of Formula I encompass two embodiments, i.e.,

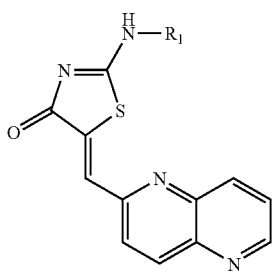

wherein $R_1$ is as above; and

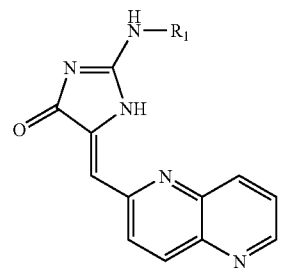

wherein $R_1$ is as above.

The compounds of Formula I-C encompass two embodiments:

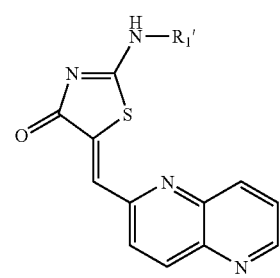

wherein $R_1'$ is as above, and

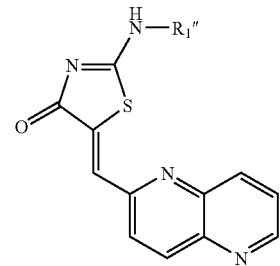

wherein $R_1''$ is as above.

The compounds of Formula I-D encompass two embodiments, i.e.

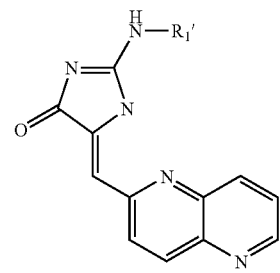

wherein $R_1'$ is as above; and

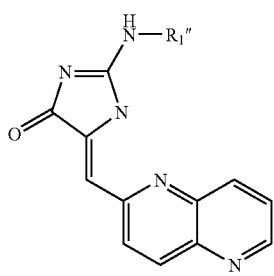

wherein $R_1''$ is as above.

In accordance with this invention, the compounds of Formulas I-C, I-C1 and I-C2 can be prepared from a compound of the formula:

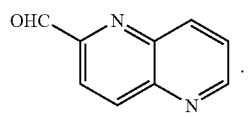

The compound of Formula II is converted to the compounds of Formulas I-C which includes the compounds of Formula I-C1 and I-C2 via the following reaction scheme.

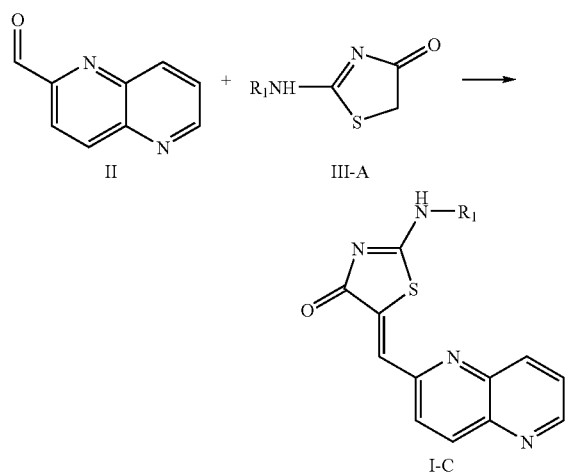

wherein $R_1$ is as above.

The reaction of the compound of Formula IIIA with the compound of Formula II to produce the compound of Formula I-C, is carried out in a high boiling organic solvent such as benzene or toluene at high temperature of from 100° C. to 200° C. in a closed system. In this manner this reaction is carried out under high temperatures and pressure. This reaction is specifically advantageous where it is desired to prepare compounds of Formula I-C where the $R_1$ group contains halogens in either in the chain X in the ring P. The compound of Formula III-A can be directly formed by reacting rhodanine with R1-NH2 by means of the following reaction scheme:

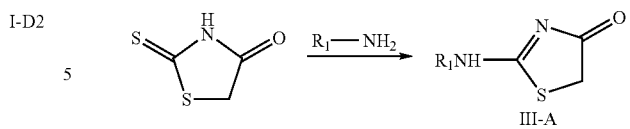

wherein $R_1$ is as above.

The compounds of Formula I-A, which includes the compounds of Formulas I-D1 and I-D2 is prepared from a

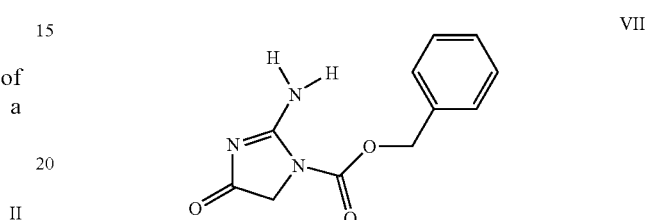

Utilizing the compound of Formula VII as a starting material, the compounds of Formula I-D are prepared by means of the following reaction scheme.

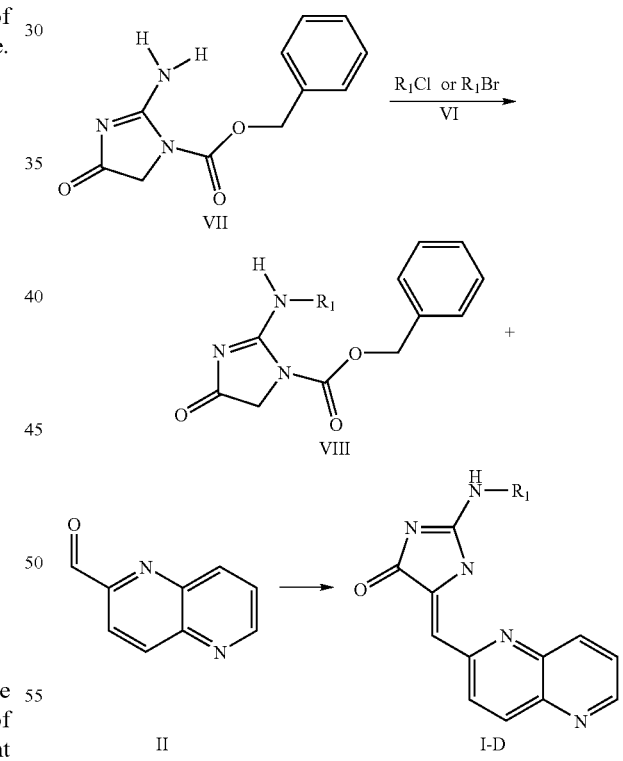

The compound of Formula VII is reacted with the compound of Formula VI to form the compound of Formula VIII by any conventional method of converting a primary amine to a secondary amine or amide by reaction of an alkyl or cycloalkyl halide or an acid halide with a primary amine. The compound of Formula VIII is reacted with a compound of Formula II to form the compound of Formula I-D by means of the Knoevenegel reaction in the manner hereto before described in connection with the reaction of a compound of Formula III-A and II to form the compound of Formula I-C.

Where the ring Ⓟ is an N-oxide of a nitrogen atom in a nitrogen containing ring which forms the ring Ⓟ, these N-oxides can be formed from a tertiary ring nitrogen atom by oxidation. Any conventional method of oxidizing a tertiary nitrogen atom to an N-oxide can be utilized. The preferred oxidizing agent is metachloroperbenzoic acid (MCPBA).

In the compound of Formulas I, I-A, I-C1 and I-D1, $R_1$ and $R_1'$ are preferably hydrogen, lower alkyl, cyclolower lower-alkyl, especially cyclopropyl,

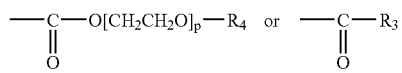

where $R_3$ and $R_4$ are as above and p is preferably 0.

In the compound of Formulas I, I-B, I-C2 and I-D2, n is preferably 1. In this case,

is preferably phenyl or a 4 to 6-membered heteroaromatic ring containing from 1 to 2 heteroatoms selected from the group consisting of nitrogen, oxygen or sulfur.

In the compounds of Formula 1B, which includes compounds of Formula I-D2 and I-C2 where $R_1''$ is $R_2-(X)_n$, n can be 1 or 2. Where n is 0, a preferred class of compounds are those compounds where Ⓟ is phenyl. The preferred class of compounds where n is 0 and $R_2$ is phenyl are those compounds where $R_5$ and $R_6$ are either both hydrogen or one of $R_5$ and $R_6$ is hydrogen and the other is halogen, lower alkoxy or lower alkyl or both $R_5$ and $R_6$ are halo or perfluoro lower alkyl.

Another preferred class of the compounds of Formula 1B are those where $R_1''$ is $R_2-(X)_n$ and n is 1. Included within this class of compounds are those compounds where X is cyclo lower alkylene preferably cyclopropylene. With respect to this class of compound wherein n is 1 and X is cyclo lower alkylene, are included those compounds where Ⓟ is phenyl and $R_5$ and $R_6$ are both hydrogen or one of $R_5$ and $R_6$ is hydrogen and the other is lower alkyl. Another class of the compounds of Formula 1B where $R_2$ is phenyl are those compounds where $R_5$ and $R_6$ are hydrogen or halogen or perfluoro lower alkyl with at least one of $R_5$ and $R_6$ being halogen or perfluoro lower alkyl. In accordance with another embodiment of invention are those preferred compounds of Formula 1B where n is 1 and X is lower alkylene. Among the preferred embodiments of this class of compounds are the compounds where $R_2$ is

and the

is phenyl. With respect to this embodiment of the invention, the preferred embodiments are those compounds where $R_5$ and $R_6$ are both hydrogen, or $R_5$ and $R_6$ are hydrogen or lower alkyl, perfluoro lower alkyl or halogen with at least one of $R_5$ and $R_6$ being other than hydrogen. Another class of compounds of Formula 1-B where n is 1 and X is lower alkylene are those compounds where Ⓟ is a heteroaromatic ring containing from 1 to 2 hetero atoms selected from the group consisting of oxygen, nitrogen and sulfur. Among the preferred compounds of the class of compounds where

is a heteroaromatic ring are those heteroaromatic rings which contain 1 hetero atom preferably sulfur. In this case, $R_5$ and $R_6$ are preferably both hydrogen or one of $R_5$ and $R_6$ can be hydrogen and the other halogen, perfluoro lower alkyl or lower alkyl.

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of the protein kinases CDK1. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of CDK1 protein kinase includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The present invention is further directed to methods of modulating or inhibiting protein kinase CDK1 activity, for example in mammalian tissue, by administering the inventive agent. The activity of agents as anti-proliferatives is easily measured by known methods, for example by using whole cell cultures in an MTT assay. The activity of the inventive agents as modulators of CDK1 protein kinase activity may be measured by any of the methods available to those skilled in the art, including in vivo and/or in vitro assays. Examples of suitable assays for activity measurements include those described in International Publication No. WO 99/21845; Parast et al., Biochemistry, 37, 16788-16801 (1998); Connell-Crowley and Harpes, Cell Cycle: Materials and Methods, (Michele Pagano, ed. Springer, Berlin, Germany)(1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methyl methacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid. If a soluble salt form is not available, the agent may be dissolved in a suitable cosolvent or combinations of cosolvents.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage determination tests in view of the experimental data for an agent.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores.

EXAMPLES

Example 1

2-Methyl-[1,5]naphthyridine

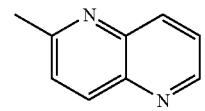

The suspension of 5-amino-2-picoline (3.56 g, 33 mmol), glycerol (12.14 g, 132 mol), and concentrate $H_2SO_4$ (34.9 g, 356 mmol) in water (20 mL) was heated with oil bath at 150° C. for 7 hrs. After cooling to room temperature, the reaction mixture was poured into 200 mL water, and 100 mL AtOEt was added. The mixture was cooled in ice bath and adjusted pH to 13 with 4.0 N NaOH to give a suspension. The solid was collected by filtration, washed with AtOEt. The filtrate was extracted with AtOEt (5×150 mL) and the combined organic layer was washed with brine and dried over $Na_2SO_4$ to give a dark brown oil (5.3 g) which was then purified by Biotage column, eluting with a gradient of 2% $CH_2Cl_2$ in MeOH to give 2-methyl-[1,5]naphthyridine (2.5 g, 52.6%) as a brown solid, which was used in the next step without further purification.

Example 2

[1, 5]Naphthyridine-2-carbaldehyde

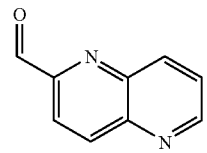

To a solution of 2-methyl-1,5-naphthyridine (216.0 mg, 1.5 mmol) in 1,4-dioxane (5 mL) was added $SeO_2$ (183.0 mg, 1.65 mmol) and the reaction mixture was refluxed for 0.5 hr, when the TLC showed no starting material left, then cooled to room temperature and filtered through celite. The solvent was removed under reduced pressure and the residue was purified by Biotage column (AcOEt: nHex=3:1) to give [1,5]naphthyridine-2-carbaldehyde as a white solid (142.3 mg, 60.0). LR-ES m/e 159 (MH+).

Example 3

(5-[1,5]Naphthyridin-2-ylmethylene-4-oxo-4,5-dihydro-thiazol-2-yl)-carbamic acid tert-butyl ester

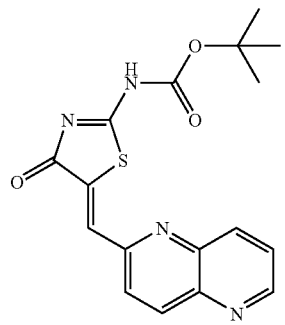

To a suspension of N-boc-pseudothiohydantoin (43.3 mg, 0.2 mmol), and 1,5-naphthyridine-6-carboxaldehyde (34.8 mg, 0.22 mmol) in toluene in a microwave tube was added benzoic acid and piperidine. The reaction mixture was heated to give a light yellow solution and then heated to 120° C. with microwave for 10 min. The reaction mixture was then cooled to r.t. and diluted with toluene. The solid was collected by filtration and washed with toluene, acetone and ether to give (5-[1,5]Naphthyridin-2-ylmethylene-4-oxo-4,5-dihydro-thiazol-2-yl)-carbamic acid tert-butyl ester as a light yellow solid: 48.6 mg (68.1%), HR-ES (+) m/e calcd. for $C_{17}H_{16}N_4O_3S$: (M+H)+ 357.1016. Found: 357.1015.

Example 4

2-Amino-5-[1,5]naphthyridin-2-ylmethylene-thiazol-4-one

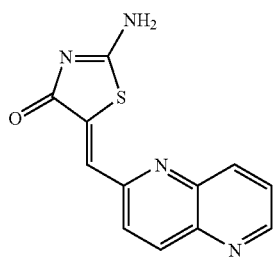

A suspension of (5-[1,5] Naphthyridin-2-ylmethylene-4-oxo-4,5-dihydro-thiazol-2-yl)-carbamic acid tert-butyl ester (20.0 mg, 0.056 mmol) in xylenes (1 mL) in a microwave tube was heated to give a light yellow solution and then heated to 170° C. with microwave for 1 hr. The reaction mixture was then cooled to r.t. and diluted with toluene. The solid was collected by filtration and washed with toluene, acetone and ether to give 2-Amino-5-[1,5]naphthyridin-2-ylmethylene-thiazol-4-one as a light yellow solid: 5.6 mg (39.2%), HR-ES (+) m/e calcd. for $C_{12}H_8N_4OS$: (M+H)+ 256.0419. Found: 256.0422.

Example 5

5-[1,5]Naphthyridin-2-ylmethylene-2-(2-phenyl-cyclopropylamino)-thiazo-1-4-one

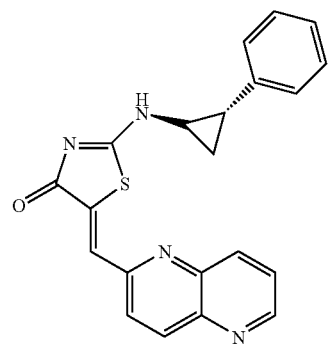

To a suspension of 2-(trans)-phenylcyclopylamino-thiazol-4-one (38.0 mg, 0.16 mmol), and 1,5-naphthyridine-6-carboxaldehyde (31.6 mg, 0.20 mmol) in toluene (1 mL) in a microwave tube were added benzoic acid (2.0 mg, 0.02 mmol) and piperidine (1.7 uM, 0.02 mmol). The reaction mixture was heated to 150° C. with microwave for 0.5 hr. The reaction mixture was then cooled to r.t. and diluted with toluene. The solid was collected by filtration and the solid was washed with toluene, $CH_2Cl_2$ and ether to give 5-[1,5] naphthyridin-2-ylmethylene-2-(2-phenyl-cyclopropylamino)-thiazo-1-4-one as a brown solid: 21.6 mg (36.2%). HR-ES (+) m/e calcd. for $C_{21}H_{16}N_4OS$: (M+H)+ 373.1118. Found: 373.1117.

Example 6

2-(2-Chloro-benzylamino)-5-[1,5]naphthyridin-2-ylmethylene-thiazol-one

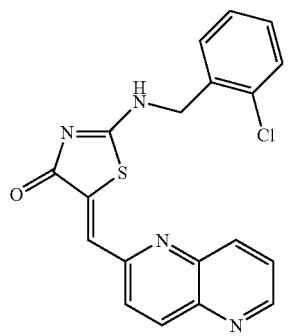

To a suspension of 2-(2-chloro-benzylamino)-thiazol-4-one (77.0 mg, 0.32 mmol), and 1,5-naphthyridine-6-carboxaldehyde (63.2 mg, 0.40 mmol) in toluene (1 mL) in a microwave tube were added benzoic acid (2.0 mg, 0.02 mmol) and piperidine (1.7 uM, 0.02 mmol). The reaction mixture was heated to 150° C. with microwave for 10 min. and then cooled to r.t. The solid was filtered off, washed with toluene to give a brown solid, which was dissolved in 1 mL hot DMF and diluted with water. The precipitates were collected and washed with water, acetone and ether, dried to give 2-(2-chloro-benzylamino)-5-[1,5] naphthyridin-2-ylmethylene-thiazol-4-one as a light brown solid (45.6 mg, 37.4%). HR-ES (+) m/e calcd. for $C_{19}H_{13}ClN_4OS$: $(M+H)^+$ 381.0572. Found: 381.0572.

Example 7

2-[(3-Methyl-thiophen-2-ylmethyl)-amino]-5-[1,5]naphthyridin-2-ylmethylene-thiazol-4-one

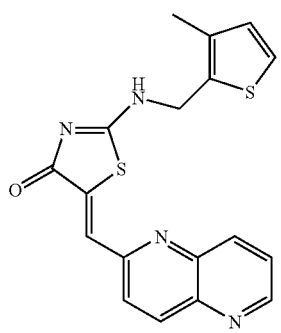

To a suspension of 2-[(3-methyl-thiophen-2-ylmethyl)-amino]-thiazol-4-one (36.2 mg, 0.16 mmol), and 1,5-naphthyridine-6-carboxaldehyde (31.6 mg, 0.20 mmol) in toluene (1 mL) in a microwave tube were added benzoic acid (2.0 mg, 0.02 mmol) and piperidine (1.7 uM, 0.02 mmol). The reaction mixture was heated to 130° C. with microwave for 10 min. The reaction mixture was then cooled to r.t. and diluted with toluene. The solid was collected by filtration and the solid was washed with toluene, MeOH and ether to give 2-[(3-Methyl-thiophen-2-ylmethyl)-amino]-5-[1,5]naphthyridin-2-ylmethylene-thiazol-4-one as a light brown solid (25.7 mg, 43.9%). HR-ES (+) m/e calcd. for $C_{18}H_{14}N_4OS_2$: $(M+H)^+$ 367.0682. Found: 367.0683.

Example 8

2-(3-Chloro-4-fluoro-benzylamino)-5-[1,5]naphthyridin-2-ylmethylene-thiazol-4-one

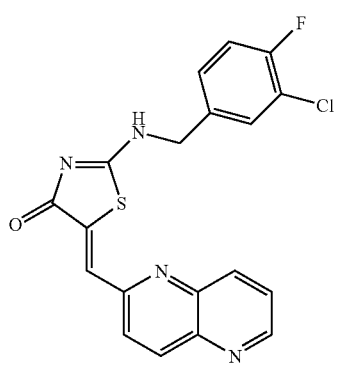

To a suspension of 2-(3-chloro-4-fluoro-benzylamino)-thiazol-4-one (41.4 mg, 0.16 mmol), and 1,5-naphthyridine-6-carboxaldehyde (31.6 mg, 0.20 mmol) in toluene (1 mL) in a microwave tube were added benzoic acid (2.0 mg, 0.02 mmol) and piperidine (1.7 uM, 0.02 mmol). The reaction mixture was heated to 130° C. with microwave for 10 min. The reaction mixture was then cooled to r.t. and diluted with toluene. The solid was collected by filtration and washed with toluene, MeOH and ether to give a brown solid: 32.6 mg (51.1%), which was dissolved in 0.5 mL hot DMF and diluted with water. The precipitates were collected and washed with water, acetone and ether, dried to give 2-(3-chloro-4-fluoro-benzylamino)-5-[1,5]naphthyridin-2-ylmethylene-thiazol-4-one as a light brown solid (18.6 mg, 29.2%). HR-ES (+) m/e calcd. for $C_{19}H_{12}ClFN_4OS$: $(M+H)^+$ 399.0477. Found: 399.0477.

Example 9

5-[1,5]Naphthyridin-2-ylmethylene-2-[(thiophen-2-ylmethyl)-amino]-thiazolone

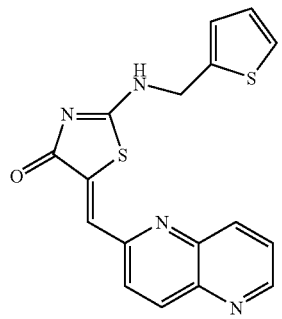

To a suspension of 2-[(thiophen-2-ylmethyl)-amino]-thiazol-4-one (34.0 mg, 0.16 mmol), and 1,5-naphthyridine-6-carboxaldehyde (31.6 mg, 0.2 mmol) in toluene (1 mL) in a microwave tube were added benzoic acid (2.0 mg, 0.02 mmol) and piperidine (1.7 uM, 0.02 mmol). The reaction mixture was heated to 120° C. with microwave for 5 min, then cooled to r.t. and diluted with toluene. The solid was collected by filtration and washed with toluene, MeOH and ether to give 5-[1,5]naphthyridin-2-ylmethylene-2-[(thiophen-2-ylmethyl)-amino]-thiazol-4-one as a light brown solid (19.7 mg, 34.9%). HR-ES (+) m/e calcd. for $C_{17}H_{12}N_4OS_2$: $(M+H)^+$ 353.0526. Found: 353.0526.

Example 10

2-[2-(3-Fluoro-phenyl)-ethylamino]-5-[1,5]naphthyridin-2-ylmethylene-thiazol-4-one

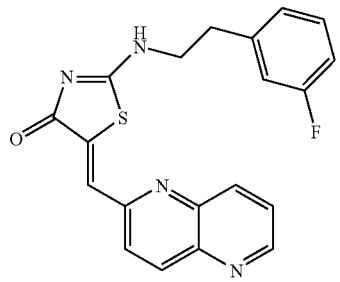

To a suspension of 2-[2-(3-fluoro-phenyl)-ethylamino]-thiazol-4-one (38.1 mg, 0.16 mmol), and 1,5-naphthyridine-6-carboxaldehyde (31.6 mg, 0.2 mmol) in toluene (1 mL) in a microwave tube were added benzoic acid (2.0 mg, 0.02 mmol) and piperidine (1.7 uM, 0.02 mmol). The reaction mixture was heated to 130° C. with microwave for 10 min., then cooled to r.t. and diluted with toluene. The solid was collected by filtration and washed with toluene, MeOH and ether to give 2-[2-(3-fluoro-phenyl)-ethylamino]-5-[1,5] naphthyridin-2-ylmethylene-thiazol-4-one as a brown solid (22.3 mg, 36.9%). HR-ES (+) m/e calcd. for $C_{20}H_{15}FN_4OS$: (M+H)$^+$ 379.1024. Found: 379.1024.

Example 11

2-[(5-Methyl-pyrazin-2-ylmethyl)-amino]-5-[1,5]naphthyridin-2-ylmethylene-thiazol-4-one

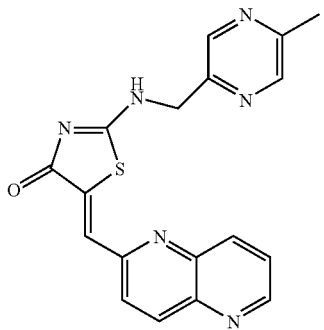

To a suspension of 2-[(5-methyl-pyrazin-2-ylmethyl)-amino]-thiazol-4-one (35.6 mg, 0.16 mmol), and 1,5-naphthyridine-6-carboxaldehyde (31.6 mg, 0.2 mmol) in toluene (1 mL) in a microwave tube were added benzoic acid (2.0 mg, 0.02 mmol) and piperidine (1.7 uM, 0.02 mmol). The reaction mixture was heated to 130° C. with microwave for 10 min., then cooled to r.t. and diluted with toluene. The solid was collected by filtration and washed with toluene, MeOH and ether to give 2-[(5-methyl-pyrazin-2-ylmethyl)-amino]-5-[1,5] naphthyridin-2-ylmethylene-thiazol-4-one as a brown solid (10.6 mg, 18.3%). HR-ES (+) m/e calcd. for $C_{18}H_{14}N_6OS$: (M+H)$^+$ 363.1023. Found: 363.1022.

Example 12

2-(2-Chloro-6-methyl-benzylamino)-5-[1,5]naphthyridin-2-ylmethylene-thiazol-4-one

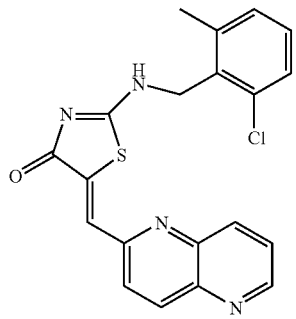

To a suspension of 2-(2-chloro-6-methyl-benzylamino)-thiazol-4-one (40.8 mg, 0.16 mmol), and 1,5-naphthyridine-6-carboxaldehyde (31.6 mg, 0.2 mmol) in toluene (1 mL) in a microwave tube were added benzoic acid (2.0 mg, 0.02 mmol) and piperidine (1.7 uM, 0.02 mmol). The reaction mixture was heated to 130° C. with microwave for 15 min., then cooled to r.t. and diluted with toluene. The solid was collected by filtration and washed with toluene, MeOH and ether to give 2-(2-chloro-6-methyl-benzylamino)-5-[1,5] naphthyridin-2-ylmethylene-thiazol-4-one as a brown solid (32.9 mg, 52.1%). HR-ES (+) m/e calcd. for $C_{20}H_{15}ClN_4OS$: (M+H)$^+$ 395.0728. Found: 395.0728.

Example 13

2-(2-Chloro-4-fluoro-benzylamino)-5-[1,5]naphthyridin-2-ylmethylene-thiazol-4-one

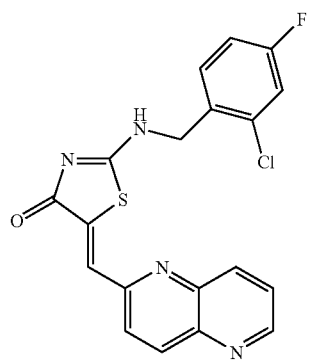

To a suspension of 2-(2-chloro-4-fluoro-benzylamino)-thiazol-4-one (41.4 mg, 0.16 mmol), and 1,5-naphthyridine-6-carboxaldehyde (31.6 mg, 0.2 mmol) in toluene (1 mL) in a microwave tube were added benzoic acid (2.0 mg, 0.02 mmol) and piperidine (1.7 uM, 0.02 mmol). The reaction mixture was heated to 130° C. with microwave for 15 min., then cooled to r.t. and diluted with toluene. The solid was collected by filtration and washed with toluene, MeOH and ether to give 2-(2-chloro-4-fluoro-benzylamino)-5-[1,5] naphthyridin-2-ylmethylene-thiazol-4-one as a brown solid (30.5 mg, 47.8%). HR-ES (+) m/e calcd. for $C_{19}H_{12}FClN_4OS$: (M+H)$^+$ 399.0477. Found: 399.0476.

Example 14

2-(2-Chloro-benzylamino)-5-[1,5]naphthyridin-2-ylmethylene-1,5-dihydro-imidazol-4-one

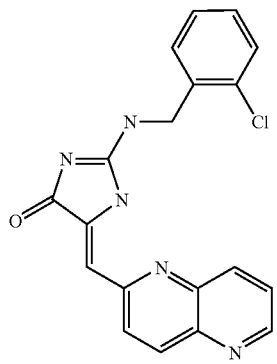

A suspension of 2-amino-4-oxo-4,5-dihydro-imidazole-1-carboxylic acid benzyl ester* (46.62 mg, 0.20 mmol), 2-chlorobenzylbromide (41.0 mg, 0.20 mmol) and K₂CO₃ (41.4 mg, 0.30 mmol) in acetonitrile (1.5 mL) was heated to reflux under argon for 3 hrs. Cooled to r.t. and the reaction mixture was partitioned between EtOAc and water. The organic layer was dried over Na₂SO₄ and concentrated to give 2-(2-chloro-benzylamino)-4-methylene-4,5-dihydro-imidazole-1-carboxylic acid benzyl ester as an oil (63.0 mg, 88.2%).

* 2-amino-4-oxo-4,5-dihydro-imidazole-1-carboxylic acid benzyl ester was prepared according to the method described by C-H Kwon et al. *J. Med. Chem.* 1991, 34,1845-1849.

To a mixture of 2-(2-chloro-benzylamino)-4-methylene-4,5-dihydro-imidazole-1-carboxylic acid benzyl ester (62.0 mg, 0.17 mmol), 1,5-naphthyridine-6-carboxaldehyde (31.6 mg, 0.2 mmol) and iPrOH (5.0 mL) in a 25-mL round bottom flask was added piperidine (0.05 mL) and the suspension was then heated under refluxing for 3.5 hrs to give a suspension. The reaction mixture was concentrated to give a brown solid which was washed with MeOH and ether. The solid was collected by filtration to give 2-(2-chloro-benzylamino)-5-[1,5]-naphthyridin-2-ylmethylene-1,5-dihydro-imidazol-4-one as a brown solid, (10.1 mg, 16.3%). HR-ES (+) m/e calcd. for C₁₉H₁₄ClN₅OS: (M+H)⁺ 364.0960. Found: 364.0959.

Example 15

(5-[1,5]Naphthyridin-2-ylmethylene-4-oxo-4,5-dihydro-1H-imidazol-2-yl) -carbamic acid tert-butyl ester

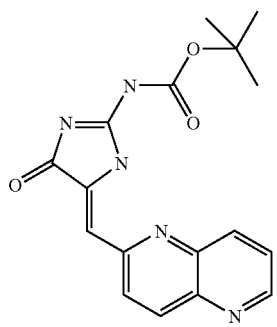

A suspension of 2-amino-4-oxo-4,5-dihydro-imidazole-1-carboxylic acid benzyl ester (46.6 mg, 0.20 mmol), Boc₂O (52.3 mg, 0.24 mmol) and DMAP (2.5 mg, 0.02 mmol) in acetonitrile (1.5 mL) was heated to reflux under argon for 1 hr. Cooled to r.t., the reaction mixture was concentrated and the residue was partitioned between EtOAc and water. The organic layer was dried over Na₂SO₄ and concentrated to give 2-tert-butoxycarbonylamino-4-oxo-4,5-dihydro-imidazole-1-carboxylic acid benzyl ester as an oil (55.0 mg, 82.6%).

To a mixture of 2-tert-butoxycarbonylamino-4-oxo-4,5-dihydro-imidazole-1-carboxylic acid benzyl ester (53.3 mg, 0.16 mmol), 1,5-naphthyridine-6-carboxaldehyde (31.6 mg, 0.2 mmol) and iPrOH (5.0 mL) in a 25-mL round bottom flask was added piperidine (0.05 mL) and the suspension was then heated under refluxing for 3 hrs to give a suspension. The reaction mixture was cooled to r.t. and the solid was collected by filtration to give (5-[1,5]-naphthyridin-2-ylmethylene-4-oxo-4,5-dihydro-1H-imidazol-2-yl)-carbamic acid tert-butyl ester as a yellow solid, 29.8 mg (54.9%). HR-ES (+) m/e calcd. for C₁₇H₁₇N₅O₃: (M+H)⁺ 340.1404. Found: 340.1404.

Example 16

N-(5-[1,5]Naphthyridin-2-ylmethylene-4-oxo-4,5-dihydro-1H-imidazol-2-yl)-acetamide

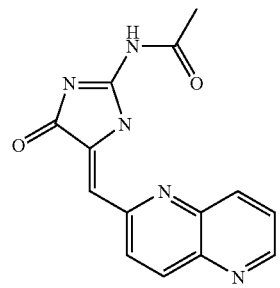

To a suspension of 2-amino-4-oxo-4,5-dihydro-imidazole-1-carboxylic acid benzyl ester (46.6 mg, 0.20 mmol), Et₃N (26.0 mg, 0.26 mmol) and DMAP (2.5 mg, 0.02 mmol) in CH₂Cl₂ (4 mL) was added dropwise Ac₂O (24.5 mg, 0.24 mmol), and the reaction mixture was then heated to reflux under argon for 1 hr. Cooled to r.t., the reaction mixture was concentrated and the residue was partitioned between EtOAc and water. The organic layer was dried over Na₂SO₄ and concentrated to give 2-acetylamino-4-oxo-4,5-dihydro-imidazole-1-carboxylic acid benzyl ester as an oil (54.0 mg, 98.2%).

To a mixture of 2-acetylamino-4-oxo-4,5-dihydro-imidazole-1-carboxylic acid benzyl ester (47.1 mg, 0.17 mmol), 1,5-naphthyridine-6-carboxaldehyde (31.6 mg, 0.2 mmol) and iPrOH (5.0 mL) in a 25-mL round bottom flask was added piperidine (0.05 mL) and the suspension was then heated under refluxing for 3 hrs to give a suspension. The reaction mixture was cooled to r.t. and the solid was collected by filtration to give N-(5-[1, 5]-naphthyridin-2-ylmethylene-4-oxo-4,5-dihydro-1H-imidazol-2-yl)-acetamide as a yellow solid, 15.3 mg (31.8%). HR-ES (+) m/e calcd. for C₁₄H₁₁N₅O₂: (M+H)⁺ 282.0986. Found: 282.0985.

Example 17

Cyclopropanecarboxylic acid (5-[1,5]naphthyridin-2-ylmethylene-4-oxo-4,5-dihydro-1H-imidazol-2-yl)-amide

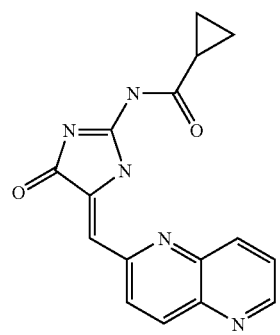

A suspension of 2-amino-4-oxo-4,5-dihydro-imidazole-1-carboxylic acid benzyl ester (100.0 mg, 0.43 mmol), cyclopropanecarbonylchloride (45.0 mg, 0.43 mmol) and Hunig's base (83.0 mg, 0.64 mmol) in acetonitrile (4 mL) was heated to reflux under argon for 0.5 hr. Cooled to r.t., the reaction mixture was concentrated and the residue was partitioned between EtOAc and water. The organic layer was dried over Na$_2$SO$_4$ and concentrated and the residue was triturated with AcOEt to give a suspension. The solid was filtered to give 2-(cyclopropanecarbonyl-amino)-4-oxo-4,5-dihydro-imidazole-1-carboxylic acid benzyl ester as an oil (113.0 mg, 87.6%).

To a mixture of 2-(cyclopropanecarbonyl-amino)-4-oxo-4,5-dihydro-imidazole-1-carboxylic acid benzyl ester (109.6 mg, 0.36 mmol), 1,5-naphthyridine-6-carboxaldehyde (47.4 mg, 0.30 mmol) and iPrOH (5.0 mL) in a 25-mL round bottom flask was added piperidine (0.05 mL) and the suspension was then heated under refluxing for 3.5 hrs to give a suspension. The reaction mixture was cooled to r.t. and the solid was collected by filtration, washed with MeOH, and ether to give cyclopropanecarboxylic acid (5-[1,5]naphthyridin-2-ylmethylene-4-oxo-4,5-dihydro-1H-imidazol-2-yl)-amide as a light brown solid, 32.6 mg (35.4%). HR-ES (+) m/e calcd. for C$_{16}$H$_{13}$N$_5$O$_2$: (M)$^+$ 307.1069. Found: 307.1066.

Example 18

2-(2-Chloro-4-fluoro-benzylamino)-5-[1,5]naphthyridin-2-ylmethylene-1,5-dihydro-imidazol-4-one

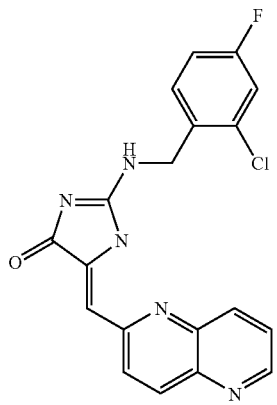

A suspension of 2-amino-4-oxo-4,5-dihydro-imidazole-1-carboxylic acid benzyl ester (93.2 mg, 0.40 mmol), 2-chloro-4-fluoro-benzylbromide (89.2 mg, 0.40 mmol) and K$_2$CO$_3$ (83.01 mg, 0.60 mmol) in acetonitrile (10 mL) was heated to reflux under argon for 1 hr. Cooled to r.t. and the reaction mixture was partitioned between EtOAc and water. The organic layer was dried over Na$_2$SO$_4$ and concentrated to give a residue which was triturated with EtOAc and filtered to give 2-(2-chloro-4-fluoro-benzylamino)-4-oxo-4,5-dihydro-imidazole-1-carboxylic acid benzyl ester as a white solid (73.0 mg, 48.7%).

To a mixture of 2-(2-chloro-4-fluoro-benzylamino)-4-oxo-4,5-dihydro-imidazole-1-carboxylic acid benzyl ester (70.1 mg, 0.19 mmol), 1,5-naphthyridine-6-carboxaldehyde (28.7 mg, 0.18 mmol) and iPrOH (5.0 mL) in a 25-mL round bottom flask was added piperidine (0.05 mL) and the suspension was then heated under refluxing for 4 hrs to give a suspension. The reaction mixture was cooled to r.t. and the solid was collected by filtration, washed with MeOH, and ether to give 2-(2-chloro-4-fluoro-benzylamino)-5-[1,5]naphthyridin-2-ylmethylene-1,5-dihydro-imidazol-4-one as a light yellow solid, 30.6 mg (43.0%). HR-ES (+) m/e calcd. for C$_{19}$H$_{13}$FClN$_5$O: (M+H)$^+$ 382.0866. Found: 382.0866.

Example 19

5-[1,5]Naphthyridin-2-ylmethylene-2-(2-trifluoromethyl-benzylamino)-1,5-dihydro-imidazol-4-one

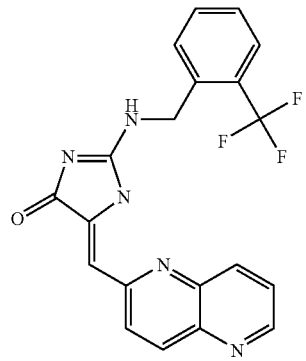

A suspension of 2-amino-4-oxo-4,5-dihydro-imidazole-1-carboxylic acid benzyl ester (93.2 mg, 0.40 mmol), 2-trifluoromethyl-benzylbromide (95.6 mg, 0.40 mmol) and K$_2$CO$_3$ (83.01 mg, 0.60 mmol) in acetonitrile (10 mL) was heated to reflux under argon for 1 hr. Cooled to r.t. and the reaction mixture was partitioned between EtOAc and water. The organic layer was dried over Na$_2$SO$_4$ and concentrated to give a residue which was triturated with EtOAc and filtered to give 4-oxo-2-(2-trifluoromethyl-benzylamino)-4,5-dihydro-imidazole-1-carboxylic acid benzyl ester as a white solid (75.0 mg, 48.1%).

To a mixture of 4-oxo-2-(2-trifluoromethyl-benzylamino)-4,5-dihydro-imidazole-1-carboxylic acid benzyl ester (70.4 mg, 0.18 mmol), 1,5-naphthyridine-6-carboxaldehyde (28.7 mg, 0.18 mmol) and iPrOH (5.0 mL) in a 25-mL round bottom flask was added piperidine (0.05 mL) and the suspension was then heated under refluxing for 4 hrs to give a suspension. The reaction mixture was cooled to r.t. and the solid was collected by filtration, washed with MeOH and ether. The solid was then re-crystallized from AcOEt-MeOH to give 5-[1,5]naphthyridin-2-ylmethylene-2-(2-trifluoromethybenzylamino)-1,5-dihydro-imidazol-4-one as a light yellow crystalline material (11.6 mg, 16.2%). HR-ES (+) m/e calcd. for C$_{20}$H$_{14}$F$_3$N$_5$O: (M+H)$^+$ 398.1223. Found: 398.1222.

Example 20

2-(2,4-Bis-trifluoromethyl-benzylamino)-5-[1,5]naphthyridin-2-ylmethylene-1,5-dihydro-imidazol-4-one

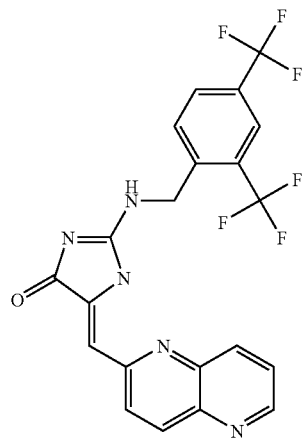

A suspension of 2-amino-4-oxo-4,5-dihydro-imidazole-1-carboxylic acid benzyl ester (93.2 mg, 0.40 mmol), 2,4-bis-trifluoromethyl-benzylbromide (126.6 mg, 0.40 mmol) and $K_2CO_3$ (83.01 mg, 0.60 mmol) in acetonitrile (10 mL) was heated to reflux under argon for 1 hr. Cooled to r.t. and the reaction mixture was partitioned between EtOAc and water. The organic layer was dried over $Na_2SO_4$ and concentrated to give a residue which was triturated with EtOAc and filtered to give 2-(2,4-bis-trifluoromethyl-benzylamino)-4-oxo-4,5-dihydro-imidazole-1-carboxylic acid benzyl ester as a white solid (96.0 mg, 52.4%).

To a mixture of 2-(2,4-bis-trifluoromethyl-benzylamino)-4-oxo-4,5-dihydro-imidazole-1-carboxylic acid benzyl ester (94.5 mg, 0.20 mmol), 1,5-naphthyridine-6-carboxaldehyde (31.7 mg, 0.20 mmol) and iPrOH (5.0 mL) in a 25-mL round bottom flask was added piperidine (0.05 mL) and the suspension was then heated under refluxing for 4.5 hrs to give a suspension. The reaction mixture was cooled to r.t. and the solid was collected by filtration, washed with MeOH, ether and dried in vacuum at 100° C. for 3 h to give 2-(2,4-bis-trifluoromethyl-benzylamino)-5-[1,5]naphthyridin-2-ylmethylene-1,5-dihydro-imidazol-4-one as a light yellow solid (21.6 mg, 23.2%). HR-ES (+) m/e calcd. for $C_{21}H_{13}F_6N_5O$: $(M+H)^+$ 466.1097. Found: 466.1098.

Example 21

3-Methyl-thiophene-2-carboxylic acid (5-[1,5]naphthyridin-2-ylmethylene-4-oxo-4,5-dihydro-1H-imidazol-2-yl)-amide

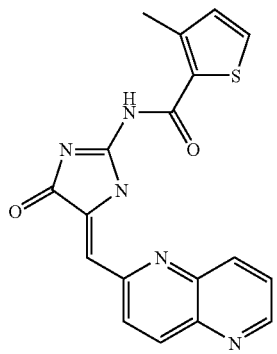

A suspension of 2-amino-4-oxo-4,5-dihydro-imidazole-1-carboxylic acid benzyl ester (93.2 mg, 0.40 mmol), 3-methylthiophene-2-carboxylchloride (64.0 mg, 0.40 mmol) and $K_2CO_3$ (83.01 mg, 0.60 mmol) in acetonitrile (10 mL) was heated to reflux under argon for 1 hr. Cooled to r.t., the reaction mixture was partitioned between EtOAc and water. The organic layer was dried over $Na_2SO_4$ and concentrated to give a solid (112 mg) which was purified by column (Biotage 40S), eluted with 50% nHex/EtOAc to give 2-[(3-methyl-thiophene-2-carbonyl)-amino]-4-oxo-4,5-dihydro-imidazole-1-carboxylic acid benzyl ester as a white solid (45.0 mg, 31.7%).

To a mixture of 2-[(3-methyl-thiophene-2-carbonyl)-amino]-4-oxo-4,5-dihydro-imidazole-1-carboxylic acid benzyl ester (42.0 mg, 0.12 mmol), 1,5-naphthyridine-6-carboxaldehyde (18.6 mg, 0.12 mmol) and iPrOH (5.0 mL) in a 25-mL round bottom flask was added piperidine (0.05 mL) and the suspension was then heated under refluxing for 4 hrs to give a suspension. The reaction mixture was cooled to r.t. and the solid was collected by filtration, washed with MeOH, and ether to give 3-methyl-thiophene-2-carboxylic acid (5-[1,5]naphthyridin-2-ylmethylene-4-oxo-4,5-dihydro-1H-imidazol-2-yl)-amide as a light yellow solid (13.3 mg, 30.5%). HR-ES (+) m/e calcd. for $C_{18}H_{13}N_5O_2S$: $(M+H)^+$ 364.0863. Found: 364.0862.

Example 22

2-(2-Methyl-benzylamino)-5-[1,5]naphthyridin-2-ylmethylene-1,5-dihydro-imidazol-4-one; compound with trifluoro-acetic acid

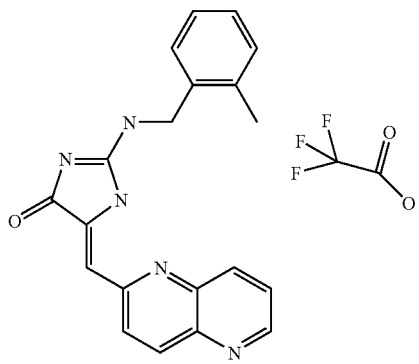

A suspension of 2-amino-4-oxo-4,5-dihydro-imidazole-1-carboxylic acid benzyl ester (93.2 mg, 0.40 mmol), alpha-bromo-o-xylene (74.02 mg, 0.40 mmol) and $K_2CO_3$ (166.0 mg, 1.20 mmol) in acetonitrile (10 mL) was heated to reflux under argon for 1 hr. Cool to r.t., the reaction mixture was partitioned between EtOAc and water. The organic layer was dried over $Na_2SO_4$ and concentrated to give an oil which was purified by preparative TLC, eluted with 50% nHex/EtOAc to give 2-(2-methyl-benzylamino)-4-oxo-4,5-dihydro-imidazole-1-carboxylic acid benzyl ester as a white solid (58.0 mg, 42.9%).

To a mixture of 2-(2-methyl-benzylamino)-4-oxo-4,5-dihydro-imidazole-1-carboxylic acid benzyl ester (55.0 mg, 0.16 mmol), 1,5-naphthyridine-6-carboxaldehyde (28.5 mg, 0.18 mmol) and iPrOH (5.0 mL) in a 25-mL round bottom flask was added piperidine (0.05 mL) and the suspension was then heated under refluxing for 10 hrs to give a suspension. The reaction mixture was cooled to r.t. and concentrated to dry. The residue was then purified by RP-HPLC to give 2-(2-methyl-benzylamino)-5-[1,5]naphthyridin-2-ylmethylene-1,5-dihydro-imidazol-4-one; compound with trifluoro-acetic acid as a light orange solid (15.3 mg, 20.9%). HR-ES (+) m/e calcd. for $C_{20}H_{17}N_5O$: $(M+H)^+$ 344.1506. Found: 344.1506.

Example 23

2-(4-Methyl-benzylamino)-5-[1,5]naphthyridin-2-ylmethylene-1,5-dihydro-imidazol-4-one; compound with trifluoro-acetic acid

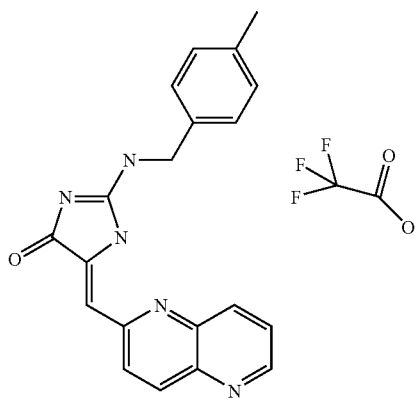

A suspension of 2-amino-4-oxo-4,5-dihydro-imidazole-1-carboxylic acid benzyl ester (93.2 mg, 0.40 mmol), alpha-bromo-p-xylene (74.02 mg, 0.40 mmol) and $K_2CO_3$ (83.01 mg, 0.60 mmol) in acetonitrile (8 mL) was heated to reflux under argon for 2 hrs. Cool to r.t., the reaction mixture was partitioned between EtOAc and water. The organic layer was dried over $Na_2SO_4$ and concentrated to give an oil (140.0 mg) which was purified by preparative TLC, eluted with 50% nHex/EtOAc to give 2-(4-methyl-benzylamino)-4-oxo-4,5-dihydro-imidazole-1-carboxylic acid benzyl ester as a white solid (57.0 mg, 42.3%).

To a mixture of 2-(4-methyl-benzylamino)-4-oxo-4,5-dihydro-imidazole-1-carboxylic acid benzyl ester (55.0 mg, 0.16 mmol), 1,5-naphthyridine-6-carboxaldehyde (28.5 mg, 0.18 mmol) and iPrOH (5.0 mL) in a 25-mL round bottom flask was added piperidine (0.05 mL) and the suspension was then heated under refluxing for 6 hrs to give a suspension. The reaction mixture was cooled to r.t. and concentrated to dry. The residue was then purified by RP-HPLC to give 2-(4-methyl-benzylamino)-5-[1,5]naphthyridin-2-ylmethylene-1,5-dihydro-imidazol-4-one; compound with trifluoro-acetic acid as a light orange solid (11.0 mg, 15.0%). HR-ES (+) m/e calcd. for $C_{20}H_{17}N_5O$: $(M+H)^+$ 344.1506. Found: 344.1505.

Example 24

2-(2,4-Dimethyl-benzylamino)-5-[1, 5] naphthyridin-2-ylmethylene-1,5-dihydro-imidazol-4-one; compound with trifluoro-acetic acid

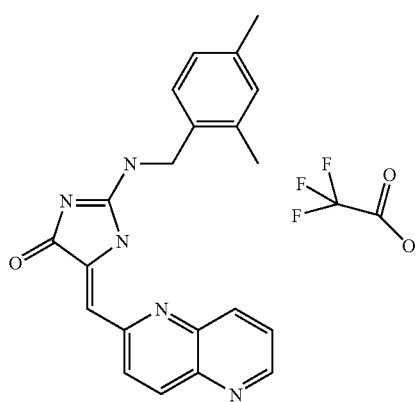

A suspension of 2-amino-4-oxo-4,5-dihydro-imidazole-1-carboxylic acid benzyl ester (93.2 mg, 0.40 mmol), 2,4-dimethylbenzylbromide (79.64 mg, 0.40 mmol) and $K_2CO_3$ (83.01 mg, 0.60 mmol) in acetonitrile (8 mL) was heated to reflux under argon for 45 min. Partition between EtOAc and water to give a suspension. Filter off the solid to give 2-(2,4-dimethyl-benzylamino)-4-oxo-4,5-dihydro-imidazole-1-carboxylic acid benzyl ester (35.0 mg). The filtrate was separated, dried to give an oil which was purified by preparative TLC, eluted with 50% nHex/EtOAc to give 60.0 mg of 2-(2, 4-dimethyl-benzylamino)-4-oxo-4,5-dihydro-imidazole-1-carboxylic acid benzyl ester as a white solid (total yield: 95.0 mg, 67.7%).

To a mixture of 2-(2,4-dimethyl-benzylamino)-4-oxo-4, 5-dihydro-imidazole-1-carboxylic acid benzyl ester (56.0 mg, 0.16 mmol), 1,5-naphthyridine-6-carboxaldehyde (28.5 mg, 0.18 mmol) and iPrOH (5.0 mL) in a 25-mL round bottom flask was added piperidine (0.05 mL) and the suspension was then heated under refluxing for 6 hrs to give a suspension. The reaction mixture was cooled to r.t. and concentrated to dry. The residue was then purified by RP-HPLC to give 2-(2,4-dimethyl-benzylamino)-5-[1,5]naphthyridin-2-ylmethylene-1,5-dihydro-imidazol-4-one; compound with trifluoro-acetic acid as a light orange solid (14.3 mg, 19.0%). HR-ES (+) m/e calcd. for $C_{21}H_{19}N_5O$: $(M+H)^+$ 358.1663. Found: 358.1663.

Example 25

2-(4-Methoxyl-benzylamino)-5-[1,5]naphthyridin-2-ylmethylene-1,5-dihydro-imidazol-4-one

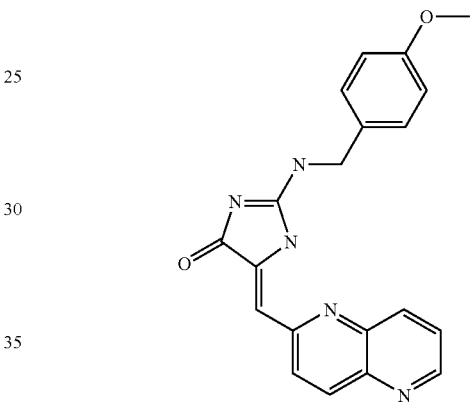

A suspension of 2-amino-4-oxo-4,5-dihydro-imidazole-1-carboxylic acid benzyl ester (93.2 mg, 0.40 mmol), 4-methoxybenzylchloride (56.24 mg, 0.40 mmol) and Hunig's base (77.40 mg, 0.60 mmol) in acetonitrile (6 mL) was heated to reflux under argon for 13 hrs. Cool to r.t., the reaction mixture was partitioned between EtOAc and water. The organic layer was dried over $Na_2SO_4$ and concentrated to give an oil which was purified by preparative TLC, eluted with 50% nHex/EtOAc to give 2-(2-methoxyl-benzylamino)-4-oxo-4,5-dihydro-imidazole-1-carboxylic acid benzyl ester as a white solid (60.0 mg, 42.5%).

To a mixture of 2-(2-methoxyl-benzylamino)-4-oxo-4,5-dihydro-imidazole-1-carboxylic acid benzyl ester (55.0 mg, 0.16 mmol), 1,5-naphthyridine-6-carboxaldehyde (28.5 mg, 0.18 mmol) and iPrOH (5.0 mL) in a 25-mL round bottom flask was added piperidine (0.05 mL) and the suspension was then heated under refluxing for 6 hrs to give a suspension. The reaction mixture was cooled to r.t. and concentrated to dry. The residue was then purified by RP-HPLC to give 2-(2-methoxyl-benzylamino)-5-[1,5]naphthyridin-2-yl-methylene-1,5-dihydro-imidazol-4-one; compound with trifluoro-acetic acid as a light orange solid (8.0 mg, 14.3%). HR-ES (+) m/e calcd. for $C_{20}H_{17}N_5O_2$: $(M+H)^+$ 360.1455. Found: 360.1456 $(MH^+)$.

Example 26

2-(4-Methoxyl-3-methyl-benzylamino)-5-[1,5]naph-thyridin-2-ylmethylene-1,5-dihydro-imidazol-4-one

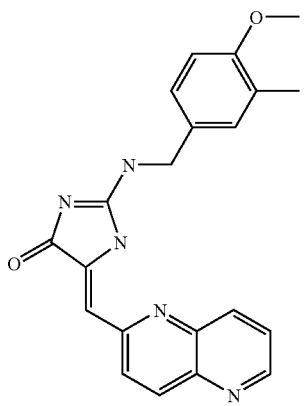

A suspension of 2-amino-4-oxo-4,5-dihydro-imidazole-1-carboxylic acid benzyl ester (93.2 mg, 0.40 mmol), 4-methoxy-3-methylbenzylchloride (68.3 mg, 0.40 mmol) and $K_2CO_3$ (83.01 mg, 0.60 mmol) in acetonitrile (6 mL) was heated to reflux under argon for 3 hrs. Cooled to r.t., the reaction mixture was partitioned between EtOAc and water. The organic layer was dried over $Na_2SO_4$ and concentrated to give a semi-solid residue 163 mg) which was purified by preparative TLC, eluted with 5% MeOH in $CH_2Cl_2$ to give 2-(2-methoxyl-4-methyl-benzylamino)-4-oxo-4,5-dihydro-imidazole-1-carboxylic acid benzyl ester as a white solid (60.0 mg, 41.0%).

To a mixture of 2-(2-methoxyl-4-methyl-benzylamino)-4-oxo-4,5-dihydro-imidazole-1-carboxylic acid benzyl ester (73.5 mg, 0.20 mmol), 1,5-naphthyridine-6-carboxaldehyde (47.5 mg, 0.30 mmol) and iPrOH (5.0 mL) in a 25-mL round bottom flask was added piperidine (0.05 mL) and the suspension was then heated under refluxing for 6 hrs to give a suspension. The reaction mixture was cooled to r.t. and concentrated to dry. The residue was then purified by RP-HPLC to give 2-(2-methoxyl-4-methyl-benzylamino)-5-[1,5]naphthyridin-2-ylmethylene-1,5-dihydro-imidazol-4-one; compound with trifluoro-acetic acid as a light orange solid (20.4 mg, 27.3%). HR-ES (+) m/e calcd. for $C_{20}H_{17}N_5O_2$: $(M+H)^+$ 360.1455. Found: 360.1456.

Example 27

The pharmacological properties of the compounds of this invention may be confirmed by a number of pharmacological assays. The exemplified pharmacological assays which follow have been carried out with the compounds according to the invention and their salts. The compounds of the invention exhibited CDK1/Cyclin B activity with Ki values of less than 5.0 µM. This demonstrates that all of these compounds were active to inhibit CDK1/Cyclin B.

Kinase Assays

To determine inhibition of CDK1 activity, either Flash-Plate™ (NEN™-Life Science Products) assay or HTRF assay was performed. Both types of kinase assays were carried out using recombinant human CDK1/Cyclin B complex. GST-cyclinB (GST-cycB) and CDK1 cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805-816). A 6×-Histidine tagged truncated form of retinoblastoma (Rb) protein (amino acid 386-928) was used as the substrate for the CDK1/Cyclin B assay (the expression plasmid was provided by Dr. Veronica Sullivan, Department of Molecular Virology, Roche Research Centre, Welwyn Garden City, United Kingdom). The Rb protein is a natural substrate for phosphorylation by CDK1 (see Herwig and Strauss Eur. J. Biochem. Vol. 246 (1997) pp. 581-601 and the references cited therein). The expression of the 62Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For the FlashPlate kinase assay, 96-well FlashPlates were coated with Rb protein at 10 µg/ml, using 100 µl per well. Plates were incubated at 4° C. overnight or at room temperature for 3 hours on a shaker. To control for nonspecific phosphorylation, one row of wells was coated with 100 µl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 µl reaction mix (25 mM HEPES, 20 mM $MgCl_2$, 0.002% Tween 20, 2 mM DTT, 1 µM ATP, 4 nM 33P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CDK1/Cyclin B, etc., was added, and "total" refers to the average counts per minute when no compound was added. The $IC_{50}$ value is the concentration of test compound that reduces by 50% the protein-kinase induced incorporation of the radiolabel under the test conditions described. The value of the inhibitor constant Ki is calculated by the following: Ki=IC50/(1+[S]/Km), where [S] is the ATP concentration and Km is Michaelis constant.

The Homogeneous Time Resolved Fluorescence (HTRF) kinase assay was carried out in 96-well polypropylene plates (BD Biosciences, Bedford, Mass.). Test compounds were first dissolved in DMSO, and then diluted in kinase assay buffer 1 (25 mM HEPES, pH7.0, 8 mM $MgCl_2$, 1.5 mM DTT, and 162 µM ATP) with DMSO concentration at 15%.

The CDK1/Cyclin B enzyme was diluted in kinase assay buffer 2 (25 mM HEPES, pH 7.0, 8 mM MgCl$_2$, 0.003% Tween 20, 0.045% BSA, 1.5 mM DTT, and 0.675 µM Rb protein). To initiate the kinase reaction, 20 µL of compound solution was mixed with 40 µL of CDK1/Cyclin B solution in assay plates with final concentration of CDK1/Cicin B and Rb at 0.1 µg/mL and 0.225 µM, respectively, and incubated at 37° C. for 30 min. 15 µL of anti-phospho-Rb (Ser 780) antibody (Cell Signaling Technology, Beverly, Mass.,) was added with a 1:7692 dilution of the antibody. Incubation was continued at 37° C. for 25 min, after which LANCE Eu-W1024 labeled anti-rabbit IgG (1 nM, PerinElmer, Wellesly, Mass.) and anti-His antibody conjugated to SureLight-Allophucocyanin (20 nM, PerkinElmer, Wellesley, Mass.) were added to the wells. Incubation was continued at 37° C. for another 40 min. At the completion of the incubation, 35 µL of reaction mixture was transferred to fresh 384-well black polystyrene plates (Corning Incorporated, Corning, N.Y.) and read on a fluorescent plate reader at excitation wavelength of 340 nm and emission wavelength of 665/615 nm.

Ki values showing CDK1/Cyclin B activity that applied to compounds of the subject matter of this invention ranges from about 0.001 µM to about 5.000 µM. Specific data for some examples are as follows:

| Example | Ki (µM) |
|---------|---------|
| 4 | 4.6729 |
| 8 | 0.2791 |
| 12 | 0.0317 |
| 16 | 1.1764 |
| 20 | 0.7350 |

What is claimed is:

1. A compound of the formula:

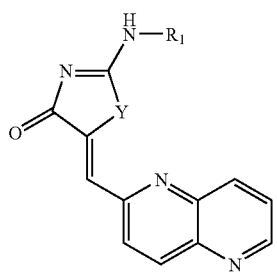

wherein

Y is —S—;

R$_1$ is a member selected from the group consisting of hydrogen, lower alkyl, cyclo lower alkyl, lower alkoxy-lower alkyl,

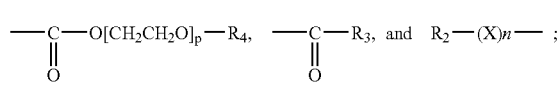

R$_3$ is a member selected from the group consisting of hydrogen, lower alkyl, cyclolower alkyl containing from 3 to 6 carbon atoms and

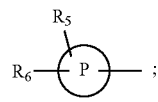

R$_4$ is a member selected from the group consisting of hydrogen and lower alkyl;

X is a member selected from the group consisting of lower alkylene, hydroxyloweralkylene, cycloloweralkylene, and mono- or di-halo lower alkylene;

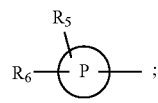

R$_2$ is

is a member selected from the group consisting of an aryl ring, a 4 to 6 membered heterocycloalkyl ring containing from 3 to 5 carbon atoms and from 1 to 2 hetero atoms selected from the group consisting of oxygen, nitrogen and sulfur, and a 5 or 6 membered heteroaromatic ring containing from 1 to 2 hetero atoms selected from the group consisting of oxygen, sulfur and nitrogen;

R$_5$ and R$_6$ are independently selected from the group consisting of hydroxy, hydroxy-lower alkyl, hydrogen, lower alkyl, halogen, perfluro lower alkyl and lower alkoxy;

n is an integer from 1 to 2; and p is an integer from 0 to 6;

and pharmaceutically acceptable salts thereof.

2. The compound of claim 1. wherein R$_1$ is hydrogen.

3. The compound of claim 2 wherein said compound is 2-amino-5-[1,5]naphthyridin-2-ylmethylene-thiazol-4-one.

4. The compound of claim 1 wherein said R$_1$ is.

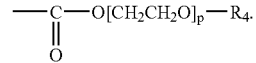

5. The compound of claim 4 wherein p is 0.

6. The compound of claim 5 wherein said compound is (5-[1,5]naphthyridin-2-ylmethylene-4-oxo-4,5-dihydro-thiazol-2-yl)-carbamic acid tert-butyl ester.

7. The compound of claim 1 wherein R$_1$ is R$_2$—(X)$_n$—.

8. The compound of claim 7 wherein

is phenyl.

9. The compound of claim 8 wherein n is 1.

10. The compound of claim 9 wherein X is cyclolower alkylene.

11. The compound of claim 10 wherein said cyclolower alkylene is cyclopropylene.

12. The compound of claim 11 wherein $R_5$ and $R_6$ are hydrogen.

13. The compound of claim 12 wherein said compound is 5-[1,5]naphthyridin-2-ylmethylene-2-(2-Phenyl-cyclopropylamino)-thiazol-4-one.

14. The compound of claim 9 wherein X is lower alkylene.

15. The compound of claim 14 wherein $R_5$ is a member selected from the group consisting of hydrogen and lower alkyl and $R_6$ is halogen.

16. The compound of claim 15 wherein said compound is 2-(2-chloro-6-methyl-benzylamino)-5-[1,5]naphthyridin-2-ylmethylene-thiazol-4-one.

17. The compound of claim 15 wherein said compound is 2-[2-(3-fluoro-phenyl)-ethylamino]-5-[1,5]naphthyridin-2-ylmethylene-thiazols-4-one.

18. The compound of claim 15 wherein said compound is 2-(2-chloro-benzylamino)-5-[1,5]naphthyridin-2-ylmethylene-thiazol-one.

19. The compound of claim 14 wherein $R_5$ and $R_6$ are halo.

20. The compound of claim 19 wherein said compound is 2-(3-chloro-4-fluoro-benzylamino)-5-[1,5]naphthyridin-2-ylmethylene-thiazol-4-one.

21. The compound of claim 19 wherein said compound is 2-(2-chloro-4-fluoro-benzylamino)-5-[1,5]naphthyridin-2-ylmethylene-thiazol-4-one.

22. The compound of claim 7 wherein

is a heteroaromatic ring containing from 1 to 2 heteroatoms selected from the group consisting of oxygen, nitrogen and sulfur.

23. The compound of claim 22 wherein said heteroaromatic ring contains 1 heteroatom.

24. The compound of claim 23 wherein said heteroatom is sulfur.

25. The compound of claim 24 wherein $R_5$ and $R_6$ are selected from the group consisting of hydrogen and lower alkyl.

26. The compound of claim 25 wherein said compound is 5-[1,5]naphthyridin-2-ylnethylene-2-[(thiophen-2-ylmethyl)-amino]-thiazolone.

27. The compound of claim 25 wherein said compound is 2-[(3-methyl-thiophen-2-ylmethyl)-amino]-5-[1,5]naphthyridin-2-ylmethylene-thiazol-4-one.

28. The compound of claim 22 wherein said heteroatoms can only be nitrogen.

29. The compound of claim 28 wherein $R_5$ and $R_6$ are independently selected from the group consisting of hydrogen and lower alkyl.

30. The compound of claim 29 wherein said compound is 2-[(5-methyf-pyrazin-2-ylmethyl)-amino]-5-[1,5]naphthyridin-2-ylmethylene-thiazol-4-one.

* * * * *